United States Patent [19]

Kamata et al.

[11] Patent Number: 5,222,114
[45] Date of Patent: Jun. 22, 1993

[54] X-RAY ANALYSIS APPARATUS, ESPECIALLY COMPUTER TOMOGRAPHY APPARATUS AND X-RAY TARGET AND COLLIMATOR THEREFOR

[75] Inventors: Shoji Kamata, Hitachi; Shigeru Izumi, Tokyo, both of Japan

[73] Assignee: Hitachi, Ltd., Tokyo, Japan

[21] Appl. No.: 706,586

[22] Filed: May 28, 1991

[30] Foreign Application Priority Data

May 30, 1990 [JP] Japan .................. 2-138227

[51] Int. Cl.$^5$ .............................. H01J 35/10
[52] U.S. Cl. .................... 378/143; 378/144; 378/125
[58] Field of Search .......... 378/4, 10, 20, 119, 378/124, 125, 126, 127, 130, 143, 144

[56] References Cited

U.S. PATENT DOCUMENTS

| | | | |
|---|---|---|---|
| 3,602,686 | 8/1971 | Lempert | 378/126 |
| 4,229,657 | 10/1980 | Bensussan et al. | 378/143 |
| 4,422,177 | 12/1983 | Mastronardi et al. | 378/10 |
| 4,573,185 | 2/1986 | Lounsberry et al. | 378/144 |
| 4,607,380 | 8/1986 | Oliver | 378/138 |

FOREIGN PATENT DOCUMENTS 57-13291 1/1982 Japan .
57-180944 11/1982 Japan .

OTHER PUBLICATIONS

"Recent Medical Diagnostic System", 1988, pp. 86-89.
Kanamori, Takahiro and Shouji Kanata, "Cross-Sectional Imaging of Large and Dense Materials by High Energy X-ray CT Using Linear Accelerator" *Journal of Nuclear Science and Technology* (Japan) 26[9], Sep. 1989, pp. 826-832.

Primary Examiner—David P. Porta
Attorney, Agent, or Firm—Antonelli, Terry, Stout & Kraus

[57] ABSTRACT

An X-ray analysis apparatus has a charged particle beam generator, an X-ray generating target bombarded by the beam and a detector for X-rays from said target transmitted by a test piece. To improve the spatial resolution of the apparatus, the beam size is reduced at the target by locating the target outside a vacuum chamber of the beam generator by providing the target as a non-circular narrow track of X-ray generating material exposed at both surfaces of the target, and by providing the beam generator with a beam accelerator and means for reducing the beam diameter between the beam accelerator and the target.

24 Claims, 7 Drawing Sheets

X-RAY ANALYSIS APPARATUS, ESPECIALLY COMPUTER TOMOGRAPHY APPARATUS AND X-RAY TARGET AND COLLIMATOR THEREFOR

BACKGROUND OF THE INVENTION

1. Field of the invention

This invention relates to X-ray analysis apparatus, particularly but not exclusively apparatus for computer tomography using X-rays, and also to X-ray targets and collimators for X-rays, for use in such X-ray apparatus. The principles of computer tomography using X-rays are well known, and need not be described here. "Computer tomography" will be abbreviated to CT, in this description.

2. Description of the prior art

Recently CT systems have been developed for the testing of products for industrial uses. Since such products, e.g. metal products, are generally high in density, testing radiations such as X-rays, gamma-rays or light rays have too low transmittance when their energy is low. Therefore, there is a need to raise the energy level of the testing radiation. Moreover, the spatial resolution sought is as high as 0.2 mm. However, when the testing radiation has high energy, problems discussed below arise, and especially high resolution is difficult of realization. These demands are high particularly for an X-ray CT system. It is now proposed to employ a charged particle beam, such as an electron beam.

As described in "Recent Medical Diagnostic Systems" (1988), pages 86–89, the typical X-ray generator of a CT system is one in which a high voltage is applied across a cathode and an anode which are arranged in the interior of a high vacuum tube, and electrodes accelerating from the cathode impinge against the X-ray generating target of the anode (in this description simply called "target") in order to generate X-rays.

U.S. Pat. No. 4,607,380 shows a rotating anode, which has customarily been used in order to reduce damage of the anode by the impinging electron beam. The beam is focussed, passes through an aperture plate and is then focussed again by focussing magnets to converge it onto the rotating anode. The anode is in a vacuum chamber connected through the aperture to the vacuum chamber containing the electron source. The X-ray are emitted from the surface of the anode which is bombarded by the electron beam. This apparatus is described as useful for the industrial inspection of objects, such as thick metal parts and achieves a small focal spot with high power output, at the anode.

U.S. Pat. No. 4,573,185 shows a rotating anode, without mentioning any particular use of it. A focal track of tungsten is arranged on a substrate and has a width narrower than that of the electron beam from the cathode, so that misalignment between the beam and the track will not affect the effective focal spot size or location.

In the Journal of Nuclear Science and Technology (Japan) 26 (1989), pages 826–832, there is described a prototype high energy X-ray CT system for use in imaging dense and large objects. A linear accelerator is employed to accelerate the electron beam and to produce X-ray photons with a maximum energy of 12 MeV. When using an X-ray source of such high energy, however, there is a problem that even a rotating anode cannot be sufficiently cooled in order to avoid damage to the surface bombarded by the energy beam.

First, problems of an X-ray generator using an electron beam will be discussed. The high energy of the X-rays signifies that the energy of the electrons is also high. The first problem of the X-ray generator is that the high energy of the electrons enlarges the size of the X-ray generation region and thereby worsens the spatial resolution. When the accelerated electrons are of at most about 200 keV, the energy levels of the generated electrons are comparatively uniform. Therefore, the electrons defocus little on the target, and the X-ray generation region of 0.2 mm has been realizable without using any special convergence means. However, when the energy of the electrons becomes 1 MeV or above, the dispersion of the energy of the electrons widens, and also the defocussing of the electrons on the target increases, so that the X-ray generation region is enlarged.

A second problem is that the vacuum performance of the X-ray generator degrades, so the necessary spatial resolution fails to be achieved. In the prior art, the entire target is made up of an X-ray generating target element of insufficient heat transfer coefficient. Besides, in the prior art, the target is installed in the same vacuum as that of the device for generating the electrons. Consequently, the large amounts of gases produced from the bombarded part (namely, X-ray generating region) of the target, when the electrons have high energy, degrades the vacuum performance of the X-ray generator. When the vacuum is degraded, the generated electrons are not sufficiently accelerated on account of the gases, and the necessary energy cannot be reached. As a result, it becomes impossible to obtain X-rays having sufficient energy and to attain the necessary spatial resolution. Moreover, when the vacuum is degraded, the electrons undergo scattering due to the gases, and the X-ray generating region enlarges. In consequence of this also, spatial resolution deteriorates.

A third problem is that the efficiency of maintenance worsens. When bombarded with electrons of high energy, the target is damaged more, so that the frequency of replacement of the target rises. Nevertheless, replacement is troublesome because the target is installed within the vacuum region.

A further area where problems arise in a CT system particularly one for imaging of industrial objects, is the collimator in front of the detector. Resolution can be increased by making the slit widths thinner, provided that the intensity of the X-rays penetrating the scanned object is sufficient. In JP-A-57-1329, there is shown a collimator for a CT system having an adjustable slit width. Slits are provided in three spaced apart, superposed plates, and the middle plate is shifted in order to adjust the effective slit width. A problem which arises is that the high energy X-rays required for industrial CT may penetrate the plate, as well as the slit, leading to loss of resolution. In the field of medical CT, JP-A-57-180944 discloses a pre-collimator for the X-rays, i.e. a collimator in the path of the beam before the beam encounters the patient, in which a plurality of sets of slits are provided in a disk, and the desired set is selected by rotating the disk.

Problems arising with the collimator are as follows. In the first place, enhancement in resolution is problematic. The resolution is enhanced as the distance between the radiation source and the test piece is shortened and the distance between the test piece and the collimator (detector) can be lengthened, so far as possible in accordance with the size of the test piece. The reason is that, since the testing radiation is generally emitted radially from the radiation source, the width of the test piece to be detected by one slit of the collimator can become narrower to enhance the resolution as the former distance is shorter and the latter distance is longer. In order that the testing radiation emitted from the radiation source may pass without colliding against the collimator, also the collimator slits need to maintain a radial positional relationship with the radiation source, despite variations in the above positional relationships. This point is not taken into consideration in the prior art.

A second problem concerns space. The shielding capability of the collimator is determined by the length of the slit, namely the thickness of the collimator. The construction of JP-A-57-1329 mentioned above has the problem that the respective slit groups require lengths necessary for shielding, so a large collimator space is necessitated. When the energy of the testing radiation is high, this drawback becomes especially serious. On the other hand, in the construction of JP-A-57-180944, the slit groups are radially arranged, so that the use of space in inferior. Particularly in the case where the energy of the testing radiation is high, there is the problem that the whole system becomes heavy in weight, incurring also the enlargement of the size of a collimator driving section.

SUMMARY OF THE INVENTION

Accordingly, a first object of the present invention is to provide an X-ray analysis apparatus, particularly a CT system, of high resolution.

A second object of the present invention is to provide an X-ray analysis apparatus of high maintenance efficiency, and high target performance.

A third object of the present invention is to provide an X-ray analysis apparatus which has an adjustable collimator of small installation space.

In one aspect the invention proposes improvement of spatial resolution by reduction of beam size at the target. Thus the invention provides an X-ray analysis apparatus comprising a charged particle beam generator having a vacuum chamber and means in the vacuum chamber for generating a charged particle beam. An X-ray generating target is located outside the vacuum chamber and arranged to be bombarded by the charged particle beam so as to emit X-rays. A detector is provided for X-rays emitted by said target and transmitted through a test piece located between the target and the detector. Preferably an electron beam generator is used which may be capable of generating an electron beam having an average energy of at least 1 MeV.

The X-ray analysis apparatus may use a detector generating electrical signals or the detector may be an X-ray sensitive film, e.g. for radiography.

The vacuum chamber generally has a vacuum-retaining window through which the charged particle beam exits from the chamber. Preferably means for cooling the target, e.g. by air or water are provided.

Since a conventional fast rotating anode may be unsuitable for high energy beams, preferably the target is displaceable relative to the beam, thereby to present to the charged particle beam a fresh portion of target not previously bombarded by the particle beam. Thus the target can be displaceable relative to the charged particle beam so that analysis operations can continue even when the beam causes perforation of the target. Suitably the X-ray generating region of the target has a maximum width of 0.2 mm, or the X-ray generating target material has a width less than the diameter of the charged particle beam which bombards the target.

Furthermore, the invention provides an X-ray analysis apparatus comprising a charged particle beam generator, and an X-ray generating target having a first surface which is bombarded by the charged particle beam and a second surface opposite the first surface. The target has at least one portion of target material adapted to emit X-rays at the second surface when bombarded by the beam and exposed at both the first surface and the second surface. This portion has a narrow width relative to the width of the target and is arranged in the target as a non-circular track, as seen looking onto the first surface.

The target may comprise a matrix material, e.g. of highly thermally conductive material, in which the track is embedded and the track may have a shape selected from spiral and continuous rectangular. Alternatively the target material is provided by a plurality of wires supported in said target.

In another aspect, the invention provides for adjustment of the spatial resolution of the apparatus. Therefore, the invention also provides an X-ray analysis apparatus comprising a charged particle beam generator for generating a charged particle beam, and an X-ray generating target arranged to be bombarded by the charged particle beam so as to emit X-rays. A detector is provided for X-rays emitted by the target and transmitted through a test piece located between the target and the detector. The spacing of the target and the detector is variable. This permits adaptation of the apparatus according to the width of the test piece.

This apparatus may have a collimator for the transmitted X-rays arranged in front of the detector. The collimator has a plurality of collimating slits having axes extending in the direction of the transmitted X-rays, and further comprises means for changing the relative directions of the axes of the collimator slits. The collimator may have a plurality of movable parts providing side walls of the collimator slits and means for moving the movable parts in conjunction, so as to vary the relative directions of the slit axes.

Alternatively a collimator for the transmitted X-rays arranged in front of the detector has a plurality of exchangeable sets of collimating slits, the angle between the axes of two adjacent slits within each of the sets of slits being a constant angle, while being different as between the sets of slits.

In an X-ray computer tomography analysis apparatus comprising means for generating X-rays and directing them to a test piece, a detector for the X-rays transmitted through the test piece, means for mounting the test piece between the X-ray generating means and the detector and for rotating it relative to the X-ray generating means and the detector, a collimator for collimating the transmitted X-rays arranged in front of the detector, and data processing means for processing data from signals from the detector, the invention provides that the collimator comprises a collimator body having a plurality of collimating slits extending continuously through said body, said slits having a slit width which is changeable. This allows selection of slit width according to a desired level of spatial resolution.

The slit width may be changeable by exchanging, in the collimating position in front of the detector, at least two exchangeable sets of slits having respectively different slit widths, so that the effective slit entrance openings are changed in width and each slit has a constant width over its whole length.

Alternatively, the collimator body has two parts which are movable relatively so as to vary the slit width in such a manner that the effective slit entrance openings change in width and each slit has a constant width over its whole length. In this case the collimator preferably has means for providing a fluid shield against passage of X-rays in undesired gaps in the collimator body caused by movement of the relatively movable parts.

Also with the aim of reducing the beam size at the target, the invention provides an X-ray analysis apparatus comprising a charged particle beam generator for generating a charged particle beam and an accelerator for particles of the charged particle beam, together with an X-ray generating target arranged to be bombarded by the charged particle beam after acceleration by the accelerator, so as to emit X-rays. Means for reducing the diameter of the charged particle beam are interposed between the accelerator and the target. Preferably means for selecting the energy of the charged particle beam are interposed between the accelerator and the target.

In yet another aspect, the invention provides a target for X-ray generating apparatus adapted to be bombarded by an energy beam and having a first side at which the energy beam is incoming and opposite the first side a second side at which X-rays are emitted. The target has an element made of X-ray generating material exposed at both the first side and the second side, the element having a narrow elongate shape with its direction of elongation extending parallel to the first and second surfaces.

Preferably the element has a width of less than 1 mm in the direction transverse to its direction of elongation.

Furthermore, the invention provides a target for X-ray generating apparatus adapted to be bombarded by an energy beam and having a first side at which said energy beam is incoming and opposite the first side a second side at which X-rays are emitted. The target includes at least one wire supported in the target and at least partly consisting of X-ray generating material and being exposed at both the first side and the second side of the target.

In a further aspect, the invention provides a collimator for X-rays having a plurality of collimation slits each having a longitudinal axis, and means for changing the relative directions of the axes. Preferably, the axes when changed in direction are maintained in alignment with respective radial directions from a common point, the distance of the common point from the collimator being altered upon changing of the relative directions of the axes.

The invention also consists in a collimator for X-rays having a plurality of spaced sets of collimator slits, the slits having longitudinal axes. Within each set the longitudinal axis of each slit is at a predetermined angle with respect to the axis of each adjacent slit in that set, this predetermined angle being respectively different as between the sets of slits.

The invention yet further provides a collimator for X-rays having a plurality of collimating slits having uniform cross-sectional shape along their length. The collimator comprises a movable body which provides a side wall of each slit and is movable so as to vary the cross-sectional shape of each slit while maintaining the cross-sectional shape of each slit uniform along its length.

The invention also provides a collimator for X-rays having a plurality of sets of collimation slits. In each set the cross-sectional area of each slits is the same. The sets of slits are spaced apart from each other, and the respective cross-sectional shapes of the slits are different as between the sets of slits.

BRIEF DESCRIPTION OF THE DRAWINGS

Embodiments of the invention will now be described by way of non-limitative example with reference to the accompanying generally schematic drawings, in which.

DESCRIPTION OF THE PREFERRED EMBODIMENTS

Figure 12:
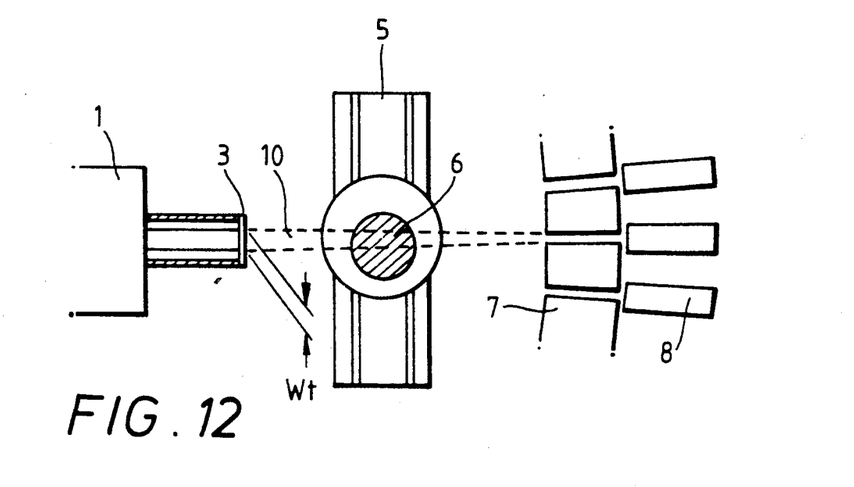
FIG. 12 is a view for explaining factors which contribute to the spatial resolution of the present invention.

First, factors contributing to spatial resolution will be described in conjunction with an X-ray CT system embodying the present invention and shown in FIG. 12 which schematically shows the relationships between an electric beam source 1 including an accelerator, a target 3 which is an X-ray source in the CT system, a test piece 6, a collimator 7 and a detector 8. X-rays are generally emitted in the shape of a fan beam, and FIG. 12 illustrates the X-ray beam entering one collimator slit. Since the X-rays impinging on the side surfaces of a slit can be neglected, the X-rays entering the detector are those emitted from a width $W_t$ on the target. The spatial resolution becomes higher with a smaller width W of the beam at the test piece. Effective measures for narrowing the width W are (a) to reduce the width $W_t$, namely, to make small the X-ray generating region on the target, (b) to reduce the width of the collimator slit, (c) to shorten the distance between the radiation source and the test piece, and (d) to lengthen the distance between the test piece and the collimator (detector). The present invention in its various aspects provides techniques providing solutions for achieving at least some of these measures.

Methods for achieving the measure (a) in which the X-ray generating region is made small are broadly classified into three. Charged particles such as electrons impinge on a target element, thereby to generate the X-rays. One aim therefore is to reduce the diameter, on the target, of the charged particles which are caused to collide against the target element. A second aim is that the width of the target element for generating the X-rays is made less than the diameter of the charged particle beam which is defined on the target. This is proposed in the prior art for a rotating anode, as mentioned. A third aim is that the vacuum of a charged particle generator is maintained in order that charged particles generated in the charged particle generator should not diverge due to their collisions with gases at a stage at which they are accelerated. Effective for this purpose is the arrangement wherein the target which is the production source of the gases is disposed outside the vacuum, namely, outside the charged particle generator. The charged particles pass outside the vacuum, but this has little effect at high energy levels. Moreover, since the target is outside the vacuum, the replacement of the target and the maintenance of a target driving device are greatly facilitated.

Next, the slit width reduction of measure (b) will be explained. Because industrial objects to be imaged vary in size, it is necessary to change the resolution by changing the slit width, in order always to achieve a good resolution for each particular object. The invention provides collimators which can achieve this.

Next, the solution of measures (c) and (d) will be explained. In this case, when the radiation source is located as near to the test piece as possible or when the collimator is located as distant from the test piece as possible, the width of the test piece as viewed from the collimator narrows, and a higher spatial resolution can be achieved. However, it may be insufficient merely to change the distance between the radiation source and the collimator (detector) in accordance with the size of the test piece. The reason therefore is that, since the testing radiation is emitted in the shape of a fan beam from the radiation source, the angle of each collimator slit needs to be controlled in accordance with the distance of the two so as to prevent the entered testing radiation from colliding against the side surfaces of the collimator. Collimators dealing with this problem are also described below.

Now, the X-ray CT system shown in FIG. 1 embodying the present invention will be described. This system has a generator and accelerator 1 which is a charged particle generator (electron beam generator) for generating and accelerating electrons and a charged particle converger 2 by which an accelerated electron beam 24 from the generator and accelerator 1 is converged on a target 3. A target moving mechanism 4 controls the impinging position of the electron beam 24 on the target 3. A CT scanner 5 scans a test piece 6 by translating and rotating it. A collimator 7 selects an X-ray beam 10 generated by the target and transmitted by the test piece 6. A detector 8 for the collimated X-ray beam 10 transmitted through the test piece 6 is located behind the collimator. The detector 8 may be a conventional one of the $CdWO_4$ scintillator type. A controller 9 controls the operations of these components. The X-ray CT system obtains the tomogram of any desired plane of the test piece 6. For this purpose the test piece 6 is scanned for translation and rotation by the CT scanner 5, the transmission of the X-ray beam through the test piece 6 in all directions is detected by the detector 8 and converted into data signals, and the transmission data items are processed according to the principle of computer tomography by data processing apparatus (not shown).

The charged particle converger 2 reduces the size of the X-ray generating region on the target 3. The charged particle converger 2 is interposed between the accelerator 1 and the target 3, and includes a plurality of convergence magnet coils 21 and a diaphragm or aperture 22 located between the convergence coils. FIG. 1 illustrates a case of two convergence magnet coils. The charged particle converger 2 is connected with the accelerator 1 so as to be kept under the same vacuum, and this vacuum is maintained by a film 23 providing an exit window on the target side thereof. Since the electron beam 24 has high energy, it is converged on the target 3 with very little attenuation even when transmitted through the film 23.

The energy of the electron beam accelerated by the accelerator 1 involves dispersion, and for example an electron beam 25 whose energy is higher or lower than specified energy is present besides the electron beam 24 of the specified energy. When the beam energy differs, a focal distance based on the convergence coil differs. That is, the electron beam of higher energy is focussed behind a target focal position, whereas the electron beam of lower energy is focussed before the target focal position. For this reason, the electron beam 25 of the unspecified energy can be eliminated by disposing the diaphragm 22 at the focal position of the electron beam 24 of the specified energy. The electron beam 24 of the specified energy is converged again by the succeeding convergence coil 21, and is focussed on the target 3. An electron beam of very small diameter can be obtained by providing a plurality of sets of the combination of the convergence coil and the diaphragm. Thus, according to this embodiment, the diameter of the electron beam to be defined on the target 3 can be reduced, so that the diameter of the X-ray beam to be generated by the target can be reduced. As a result, the test piece can be analysed at a high resolution.

Although the above embodiment is provided with the plurality of convergence coils and diaphragms, the electron beam diameter can be made smaller than in the prior art even when the electron beam is converged by the convergence coils only. Alternatively, a similar effect may be achieved when the convergence magnet coils are substituted by electrostatic lenses.

Figure 1:
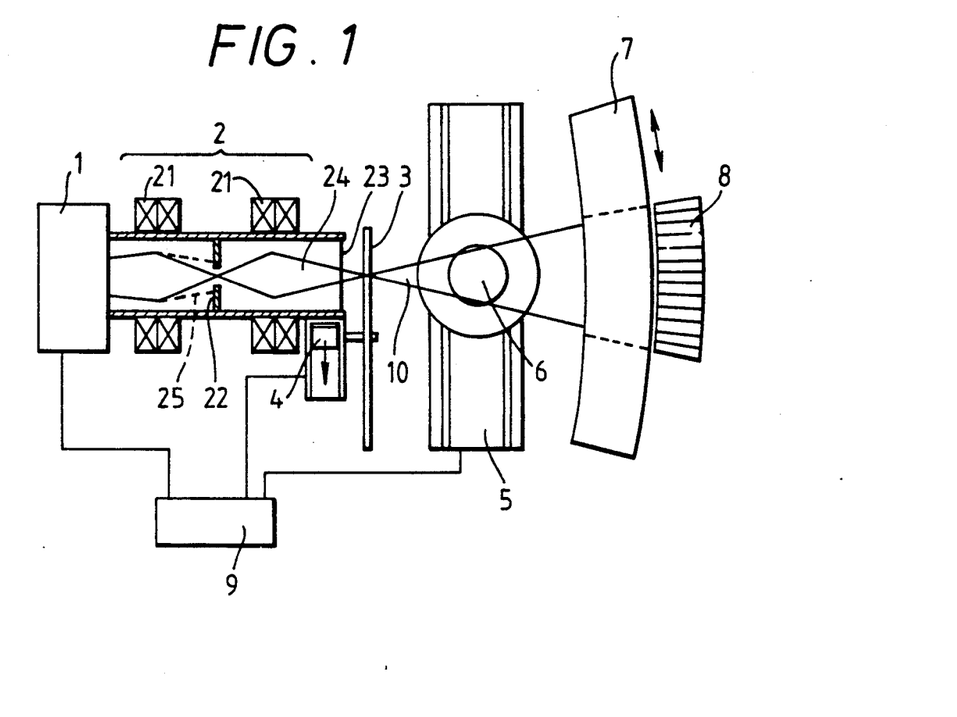
FIG. 1 is a plan view showing an embodiment of a CT system according to the present invention.

As shown in FIG. 1, the target 3 is installed in the atmospheric air outside the vacuum region of the charged particle converger 2. Accordingly, even when a large number of gas particles are produced by the collisions between the electron beam 24 and the target 3, the gases do not intrude into the generator and accelerator 1 or the charged particle converger 2, which can therefore maintain the vacuum. As a result, the electron beam 24 can assume a stable path without any influence from gases inside the generator and accelerator 1 and the charged particle converger 2. The electron beam diameter on the target can be reduced, and can be consequently made smaller than in the prior art system wherein the target is disposed within the vacuum.

Figure 2:
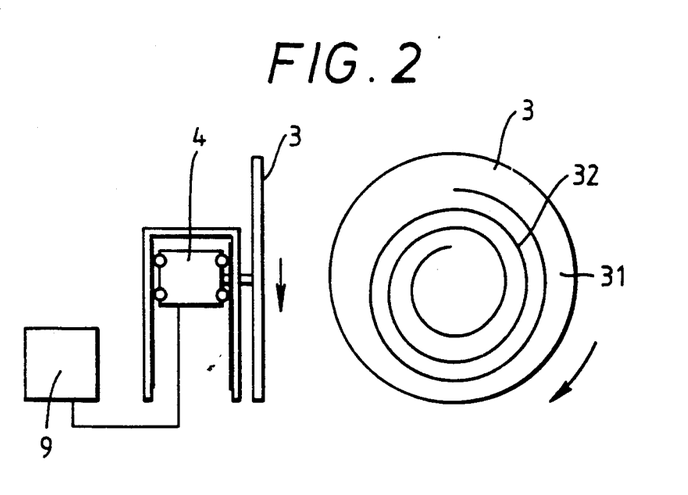
FIG. 2 is a side view showing an embodiment of the target device of the system of FIG. 1, and a face view of the target embodying the present invention.

In addition, this embodiment is equipped with the target moving mechanism 4 by which an X-ray generating target having an elongate spiral element 32 as shown in FIG. 2 is moved so as to lie in the electron beam at all times. Owing to the installation of the target outside the vacuum, the target moving mechanism 4 can be constructed, operated and maintained easily. As a result, the replacement of the target 3 and the maintenance of the target moving mechanism 4 are facilitated, and a CT system of high reliability can be provided.

Figure 3:
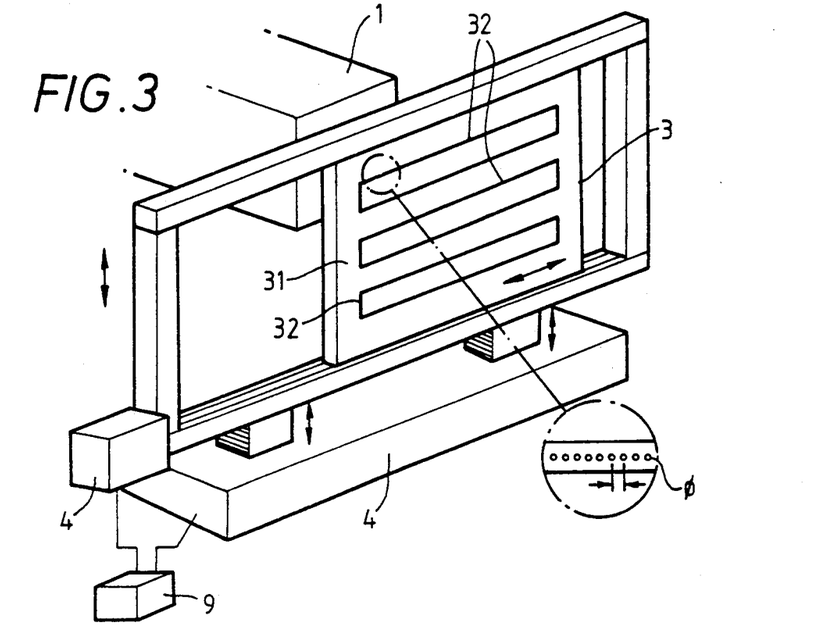
FIG. 3 is a view showing another embodiment of a target of the present invention and a target device.
Figure 4A:
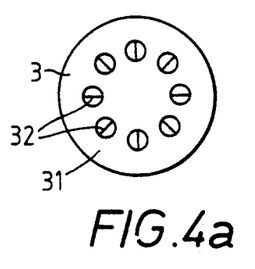
FIGS. 4(a), 4(b) and 4(c) are views showing other embodiments of the target of the invention.
Figure 4B:
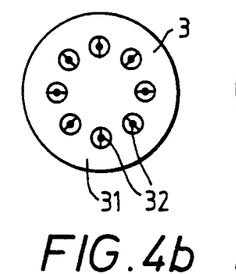
Figure 4C:
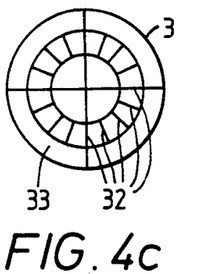

The targets of FIGS. 2 to 4 are designed for operation using the accelerated electron beams of high energy preferably employed in this invention. They differ from the rapidly rotating anode targets of the prior art in that they are moved only slowly or intermittently, because the target material is designed to be consumed. Although the target may be cooled, cooling is insufficient to prevent such consumption. Secondly, the target has a first face on which the charged particle beam impinges and an opposite, second face from which the desired X-rays are emitted towards the test piece. The target material, which in these embodiments is arranged on a narrow track which is not of continuous circular shape, is thus exposed at both faces of the target.

An embodiment where the electron energy is so high as to perforate the target will be described in more detail with reference to FIG. 3. When the diameter of the electron beam impinging on the target is small, the target is damaged. By way of example, in case of an electron beam diameter of 0.2 mm, the target material reaches a high temperature much exceeding its melting point, and it vaporizes. In view of this, the target elements 32 (e.g. of tungsten) are formed in a rectangular pattern within a target holding member 31 of high thermal conductivity, and X-rays are generated in such a manner that the target is perforated by the electron beam while being scanned vertically and laterally by the target driver 4. The case of FIG. 3 is an example in which the moving speed of the target is set at about 1-2 mm per pulse of the electron beam, and in which apertures having diameters nearly equal to the electron beam diameter of 0.2 mm are successively provided at intervals of about 1-2 mm. Thus, when the target is located outside the vacuum as stated before, the path of the electron beam is not affected even by the production of large amounts of gases due to the perforation of the target, so that the X-ray generating region can be made small to achieve a higher spatial resolution.

Next, there will be described other embodiments of the target of the present invention for making the X-ray generating region small. FIG. 2 shows one of the embodiments. The target 3 consists of a target holding member 31 made of copper or the like having a high thermal conductivity, and the spiral target element 32 made of a metal such as tungsten. The width of the target element 32 is less than the diameter of the electron beam, so that the X-ray generating region can be made small irrespective of the electron beam diameter. Moreover, since the target element 32 is held by the target holding member 31 of high thermal conductivity, heat loss from the element is facilitated to diminish the emission of gases. As a result, the consumption of the target element 32 can be suppressed to prolong the lifetime of the target, to extend the replacement term and to enhance the maintenance efficiency. Besides, owing to the suppression of the emission gases, the target 3 may sometimes be permitted to be installed within vacuum. Further, since the target element 32 is formed as a spiral track, its total length can be increased to prolong the target lifetime.

An embodiment of the target of the present invention for making the X-ray generating region still smaller will be described with reference to FIG. 4. In this embodiment, in order to further reduce the diameter or width of the region, the target element 32 has the shape of a thread or filament as shown in FIG. 4(a) or is a spot having the shape of a small ball or disc carried by a thread as shown in FIG. 4(b), or the whole target has the form of a net shown in FIG. 4(c). Thus, when the target width is set at, for example, about 0.15 mm, a high spatial resolution of 0.2 mm can be achieved, even considering the degradation of the spatial resolution attributed to the degradation of the signal processing of the detector, etc. Of course, a similar result can be achieved also by a method in which the electron beam diameter is sufficiently reduced to about 0.15 mm by the charged particle converger 2.

There will now be described embodiments of the collimators of the present invention.

Figure 5:
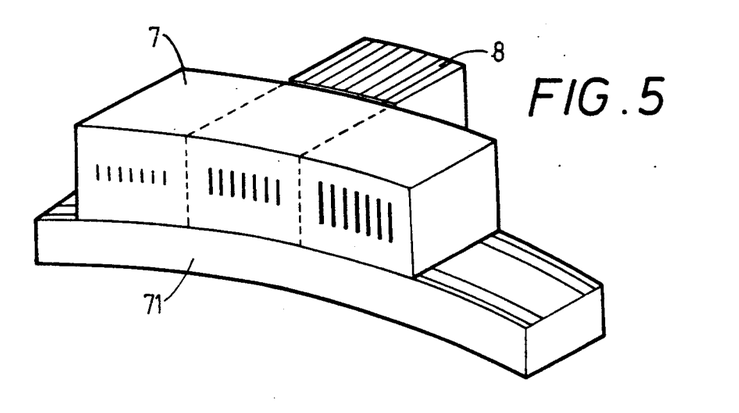
FIG. 5 is a perspective view showing a first embodiment of a collimator according to the invention.

Shown in FIG. 5 is a collimator 7 which has three sets of slits of respectively different widths and heights, and the slit groups are arrayed in one lateral row in a single block of material. The slits have a constant cross-sectional shape over their length. The number of slits in each slit group is equal to the number of the detection units of the detector 8. A desired width and height of the collimation slits can be selected from among the plurality of sets by sliding the collimator 7 laterally by means of a collimator driving mechanism 71. When the collimator slits are narrow, the collection of delicate data is realized, and the spatial resolution of a CT slice image can be heightened, but the quantity of X-rays passing through the slits is small. In addition, since the translation scanning pitch of the detector is proportional to the slit width of the collimator, the pitch of data measurement narrows, and hence, the time for the measurement increases. In contrast, when the collimator slits are broad, the time for measurement can be shortened though the spatial resolution of the tomogram is reduced. Since the slits of the collimator 7 are selected according to the purpose of the measurement of the test piece, each measurement can be performed under the best available measurement conditions, and appropriate spatial resolution can be attained. Moreover, since the slit groups are arrayed in one lateral row, it is possible to provide a CT system having the collimator of sufficient thickness (i.e. the length of the slits) so that even when the energy of X-rays is high, the volume of the collimator is small.

Figure 6:
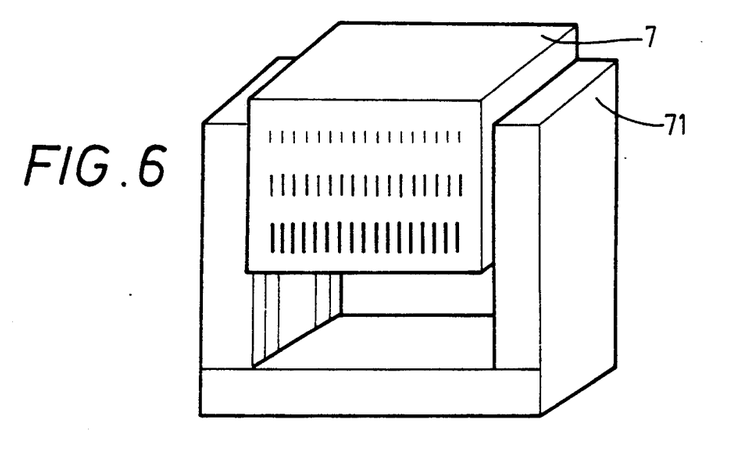
FIG. 6 is a perspective view showing a second embodiment of the collimator.

FIG. 6 shows another embodiment of the collimator 7 which has three sets of slit groups, in this case arranged in the vertical direction. As in FIG. 5, slits within each slit set have the same dimensions. A collimator driving mechanism 71 is provided through which the slit sets can be selected depending upon measurement conditions. This achieves effects similar to those of the embodiment in FIG. 5.

Figure 7A:
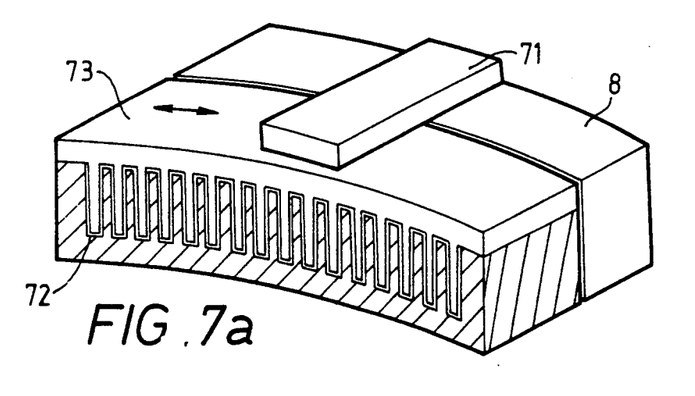
FIGS. 7(a) and 7(b) are perspective and part-sectional views showing a third embodiment of the collimator.
Figure 7B:
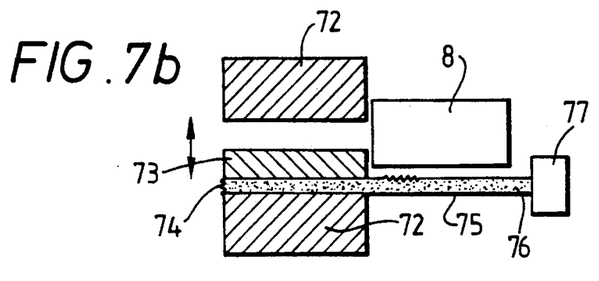

FIG. 7 shows a collimator has a structure which includes a stationary portion 72 and a movable portion 73 both having an array of projections whose side surfaces define slit walls. These slit-defining parts of the two portions are mutually inserted in interdigitated fashion. As FIG. 7(b) shows, the effective slit is one of the two slits thus formed between one projection of the portion 73 and an adjacent pair of the projections of the portion 72, since the detector element 8 is located behind this slit. Thus, the widths of the effective slits can be changed by sliding the movable portion 73 in a circular path by means of a collimator driving mechanism 71. This changes the slit opening width and the slit width uniformly along the whole length of each slit. It is consequently possible to provide the collimator which is still smaller in size than the embodiments of FIGS. 5 and 6. FIG. 7(b) shows that mercury 76 flows from a mercury trough 75 into the other, non-effective slit, shielding the detector 8 against unwanted X-rays. The mercury 76 in the mercury trough 75 is normally maintained under pressure by a pump 77 so that it flows into this clearance slit between the stationary portion 72 and the movable portion 73. A flexible seal 74 closes this clearance slit.

Figure 8A:
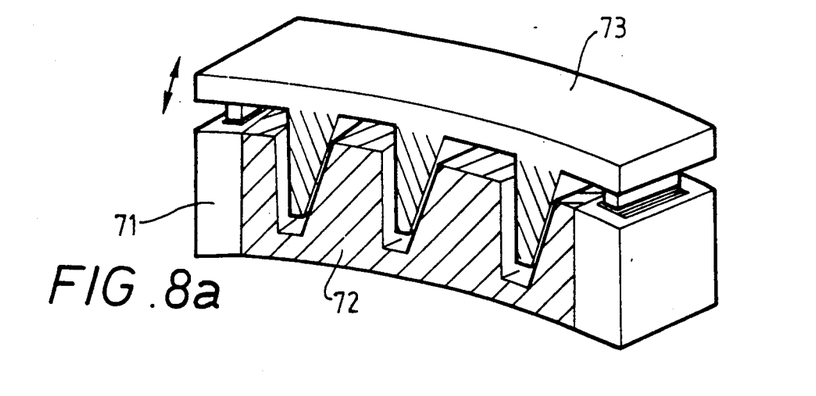
FIGS. 8(a), 8(b) and 8(c) are perspective, part-front view and part-sectional views showing a fourth embodiment of the collimator.
Figure 8B:
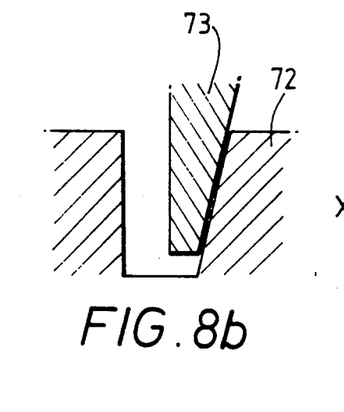
Figure 8C:
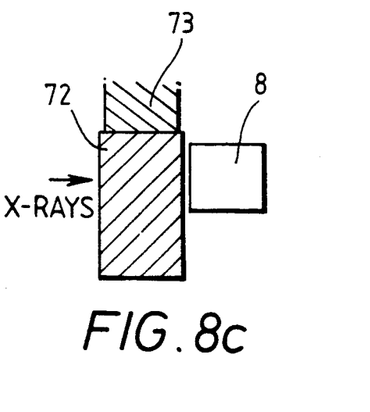

FIG. 8 shows a similar embodiment in which the collimator has a movable portion. FIG. 8(b) shows a front view, and FIG. 8(c) a part-sectional side view. This collimator has a structure which includes a stationary portion 72 and the movable portion 73 and in which the slit-defining parts of both the portions are mutually inserted in interdigitated fashion as in the preceding embodiment. One face of each of the interdigitated projections is slanting, and the respective slanting faces abut slidingly. The movable portion 73 is vertically moved by a collimator driving mechanism while the slanting surfaces slide mutually, causing lateral movement of the movable part 73 to vary the slit width uniformly over the whole length of each slit.

Figure 9A:
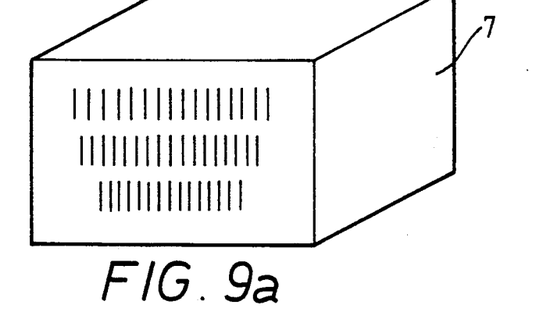
FIGS. 9(a) to (d) are diagrammatic views showing a first embodiment of a collimator in which the slit angle is variable.
Figure 9B:
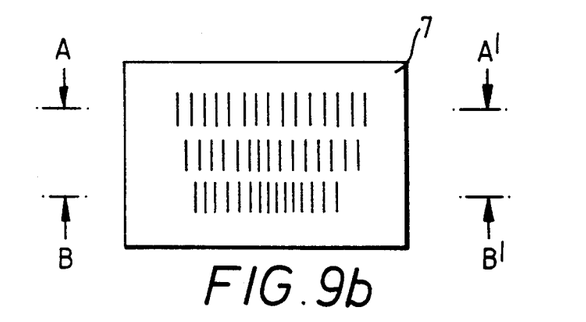
Figures 10A, 10B:
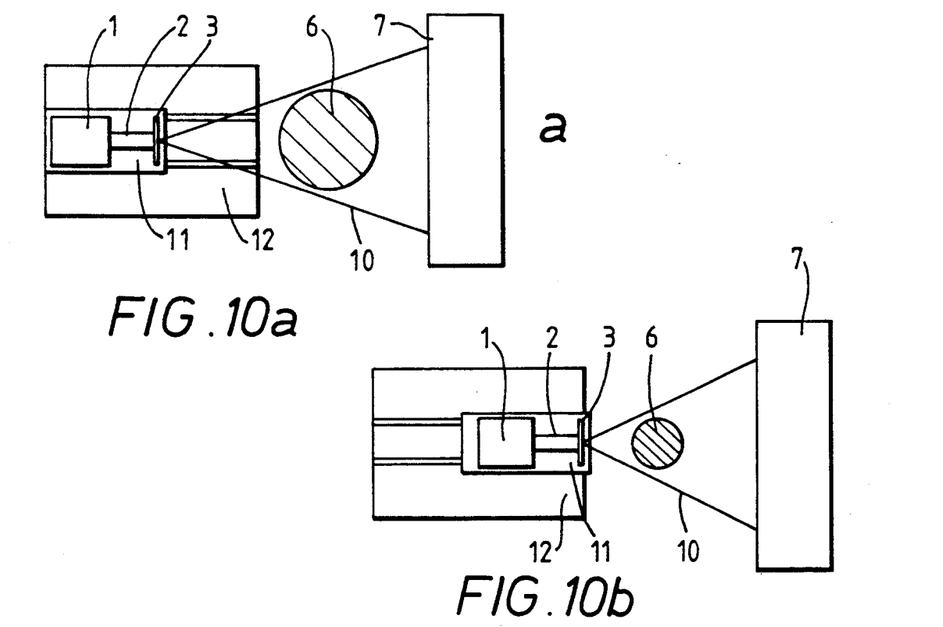
FIGS. 10(a) and 10(b) are plan views showing an embodiment of the present invention in which the distance between a test piece and the radiation source is varied.

Next, there will be described embodiments in which the slit angles of the collimator slits are varied. Before referring to FIG. 9, the reason why the angle of the collimator needs to be changed will be explained. As illustrated in FIG. 10, as the distance between the test piece 6 and the target (testing radiation source) 3 is shorter in a measurement and as the distance between the collimator 7 and the test piece 6 is longer, the width of the test piece as viewed from the slits of the collimator becomes narrower, and hence, a higher spatial resolution can be attained. In addition, the distance between the target 6 and the collimator 7 should preferably be as short as possible in order to mitigate the influences of the attenuation of the intensity of the radiation source and noise ascribable to any part other than the test piece. Accordingly, these distances are adjusted to appropriate values, depending upon the size of the test piece 6.

When the distance between the target 6 and the collimator 7 is changed in this manner, also the angle of the collimator needs to be changed. The reason is that, since the testing radiation such as X-rays generally spreads radially, the angle between the adjacent slits of the collimator needs to be changed according to the target-collimator distance as depicted in FIGS. 9(c) and 9(d), in order to prevent the testing radiation from colliding against the side surfaces of each slit.

First, the case of changing the distance between the test piece 6 and the testing radiation source, i.e. target 3, will be described in an example with reference to FIG. 10. The generator and accelerator 1, charged particle converger 2 and target 3 are fixed on a movable carriage 11, and the carriage 11 is brought towards or away from the collimator 7 by an accelerator moving mechanism 12. The carriage 11 is moved away from the collimator 7 when the test piece 6 is large as shown in FIG. 10(a), and near to the test piece 6 when the test piece 6 is small as shown in FIG. 10(b).

The collimator 7 in FIG. 9 is similar to the collimator shown in FIG. 6, and the drive mechanism thereof (not shown in FIG. 9) is the same as in FIG. 6. As in FIG. 6 there are three selectable sets of slits, and the number of slits in each slit group is equal to the number of the detection units of the detector 8. As between the different slit groups, the pitch of the slits changes on the X-ray source side, but the arrangement of the detection units of the detector does not depend upon the state of the slits and does not change because the pitch of the slits on the detector side does not change. FIGS. 9(b), (c) and (d) illustrate this. FIG. 9(b) is a face view of the block collimator and FIGS. 9(c) and (d) are respectively sectional views on the lines A–A' and B–B' showing how the angle between two adjacent slits is constant in each slit set but varies from one slit set to another.

Figure 9C:
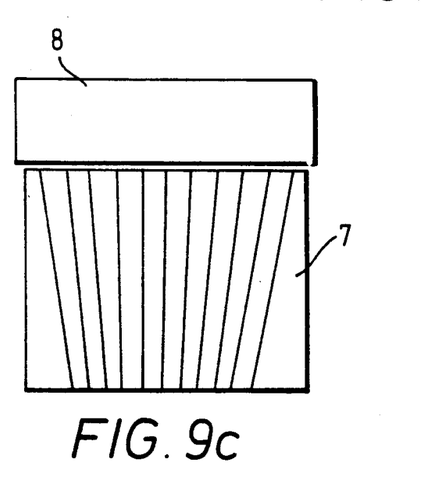
Figure 9D:
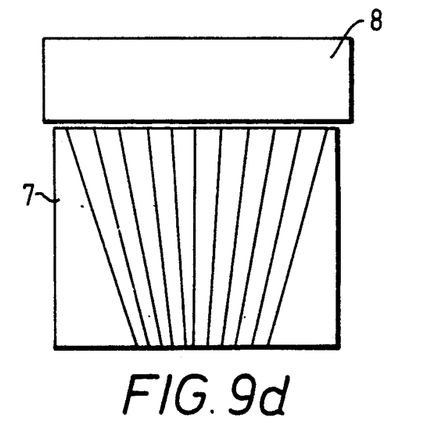

The collimator is more distant from the X-ray source when using the upper slit set (FIG. 9(c)) and nearer to the X-ray source when using the lower slit set (FIG. 9(d)). Thus, according to this embodiment, a variable spatial resolution of the system can be achieved and the installation space thereof can be saved, by changing the distance between the radiation source and the test piece or the like and then selecting the slit group which provides the collimator angle conforming to the distance.

Figure 11A:
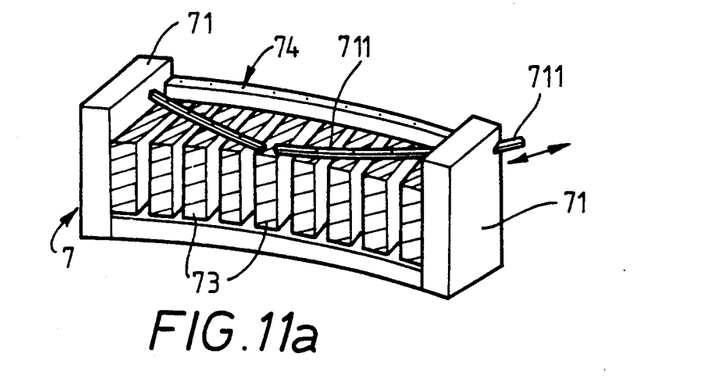
FIGS. 11(a) and 11(b) are views showing another embodiment of the collimator in which the slit angle is variable.
Figure 11B:
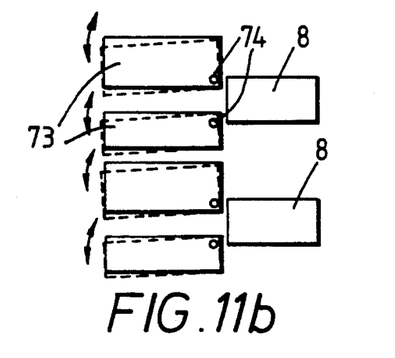

FIGS. 11(a) and 11(b) show a second collimator in which the slit angle of the collimator is variable. This collimator has its slits defined by movable portions 73 which rotate on pivots 74 on the detector side. These collimator portions 73 are moved in conjunction about the pivots 74 in the directions of the arrows in the plan view of FIG. 11(b) by a collimator driving mechanism 71, whereby the directions of slits are changed. As illustrated in FIG. 11(a), the collimator driving mechanism 71 has two drive rods 711, and the connection positions between the drive rods 711 and the individual portions 73 come closer to the pivots 74 towards two outer ends of the collimator. Accordingly, when the drive rods 711 are moved in the direction of the arrow in FIG. 11(a) by an identical distance, the amounts of movement of the respective movable collimator portions 73 are larger at the outer ends, and the changes of the angles of the slits become greater, so that the individual slits are properly directed toward the X-ray source. By this embodiment, a collimator which is small in size can be provided, and a high spatial resolution can be realized.

Figure 13:
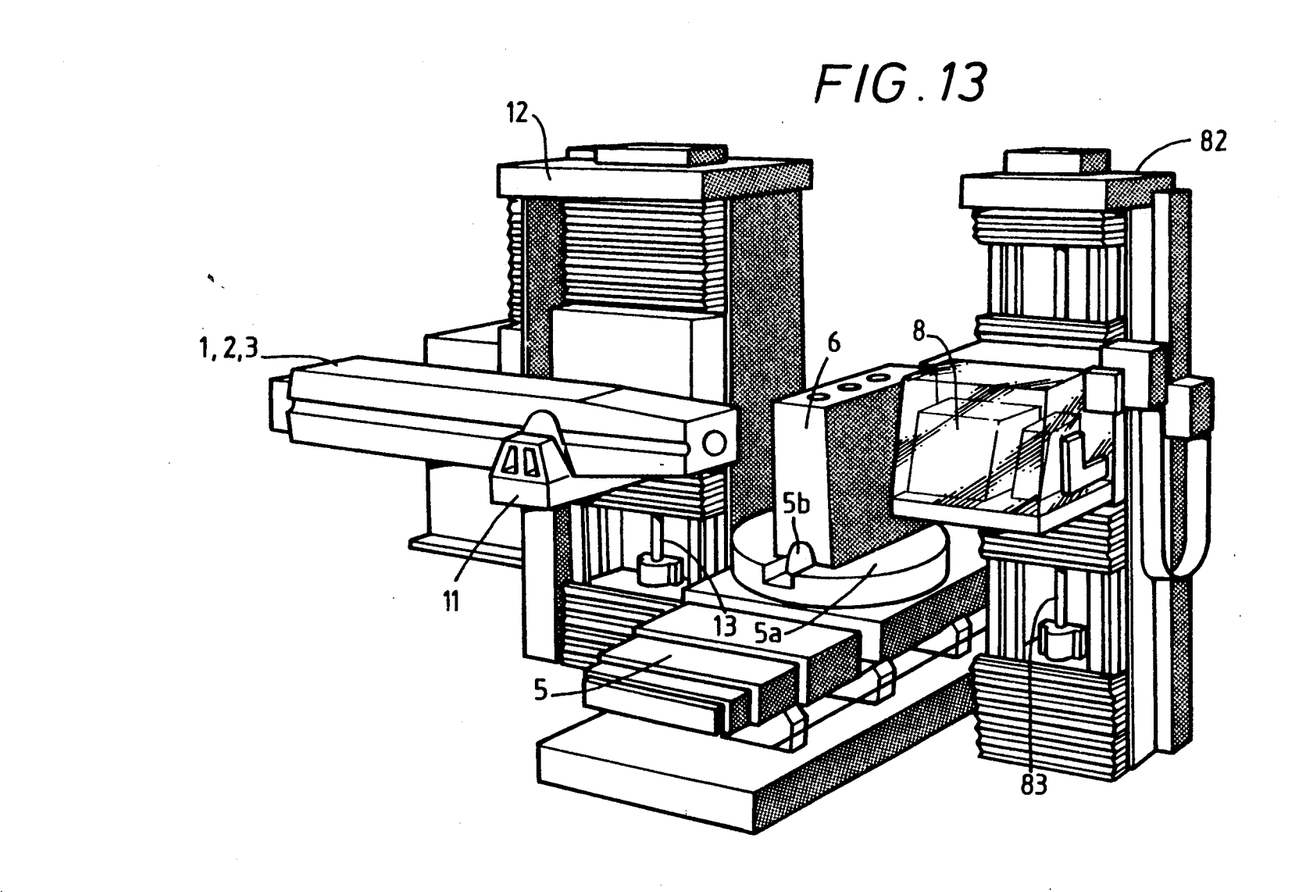
FIG. 13 is a general perspective view of an industrial CT system embodying the invention.

FIG. 13 is a perspective view of an industrial X-ray CT imaging apparatus. The test piece 6 to be analysed by CT scanning is mounted on a rotating turntable 5a which is in turn carried on a transversely movable carriage 5. A chuck 5b is shown locating the test piece 6. The electron beam generator and accelerator 1 and electron beam converger 2, together with the target 3 are mounted in a box carried on a carriage 11 which is movable vertically and horizontally towards and away from the test piece 6, in a frame 12. Likewise the detector 8 including a collimator is movable vertically in a frame 82, in order to retain its vertical position relative to the X-ray generator 1, 2, 3. Lead screws 13, 83 move the X-ray generator 1, 2, 3 and the detector 8 vertically in the frames 12, 82.

Although X-ray CT systems have thus far been described, the present invention is also applicable to other X-ray systems, e.g. transmission systems for radiography etc., wherein X-ray sensitive film is used as the detector.

Furthermore, charged particle beams other than electron beams may be used to generate the X-rays, e.g. proton beams and alpha-particle beams.

What is claimed is:

1. An X-ray analysis apparatus comprising (a) a charged particle beam generator having a vacuum chamber and means in said vacuum chamber for generating a charged particle beam, (b) an X-ray generating target located outside said vacuum chamber, said target having a first surface which is bombarded by said charged particle beam and a second surface which is opposite said first surface, said target comprising at least one portion of target material exposed at both said first surface and said second surface and which emits X-rays when said first surface is bombarded by said charged particle beam, said at least one portion having a narrow width relative to a width of said target and being arranged in said target as a non-circular track, and (c) a detector for X-rays emitted by said target and transmitted through a test piece located between said target and said detector.

2. An X-ray analysis apparatus according to claim 1 wherein said charged particle beam generator is an electron beam generator.

3. An X-ray analysis apparatus according to claim 2 wherein said electron beam generator is capable of generating an electron beam having an average energy of at least 1 MeV.

4. An X-ray analysis apparatus according to claim 1 wherein said detector produces signals in accordance with the transmitted X-rays detected, and the apparatus further comprises (d) a collimator for said transmitted X-rays located in front of said detector, (e) scanning means for rotating a said test piece relatively to said target and said detector, and (f) data processing means for processing data in signals from said detector in accordance with the principle of computer tomography.

5. An X-ray analysis apparatus according to claim 1 wherein said detector is an X-ray sensitive film.

6. An X-ray analysis apparatus according to claim 1 wherein said vacuum chamber has a vacuum-retaining window through which said charged particle beam exits from said chamber.

7. An X-ray analysis apparatus according to claim 1 further comprising means for cooling said target.

8. An X-ray analysis apparatus according to claim 7 wherein said cooling means is adapted to effect cooling of said target by air.

9. An X-ray analysis apparatus according to claim 7 wherein said cooling means is adapted to effect cooling of said target by means of liquid.

10. An X-ray analysis apparatus according to claim 1 further comprising means for displacing said target relative to the said vacuum chamber, thereby to present to said charged particle beam a fresh portion of said target not previously bombarded by said charged particle beam.

11. An X-ray analysis apparatus according to claim 10 wherein said target is displaceable relative to said charged particle beam so that analysis operations can continue even when the charged particle beam causes perforation of said target.

12. An X-ray analysis apparatus according to claim 1 wherein said charged particle beam generator is adapted to generate an electron beam having an average energy of at least 1 MeV and wherein an X-ray generating region of said target has a maximum width of 0.2 mm.

13. An X-ray analysis apparatus according to claim 1 wherein said target has an X-ray generating target material having a width less than the diameter of the charged particle beam which bombards the target.

14. A target for X-ray generating apparatus adapted to be bombarded by an energy beam and having a first side at which said energy beam is incoming and opposite said first side a second side at which X-rays are emitted when said first side is bombarded by said incoming energy beam, said target including at least one wire supported in the target and at least partly consisting of X-ray generating material and being exposed at both said first side and said second side of said target.

15. A target according to claim 14 wherein said wire has two opposite ends supported in the target and, intermediate said opposite ends thereof, said wire carries a body of said X-ray generating material.

16. An X-ray analysis apparatus comprising (a) a charged particle beam generator for generating a charged particle beam, (b) an X-ray generating target having a first surface which is bombarded by said charged particle beam and a second surface opposite said first surface, said target comprising at least one portion of target material exposed at both said first surface and said second surface and adopted to emit X-rays at said second surface when said portion exposed at said first surface is bombarded by said beam, said portion as seen looking onto said first surface, having a narrow width relative to the width of sad target and being arranged in said target as a non-circular track, and (c) a detector for X-rays emitted by said target from said second surface thereof and transmitted through a test piece located between said target and said detector.

17. An X-ray analysis apparatus according to claim 16 wherein said target comprises a matrix material in which said track is embedded and said track has a shape selected from spiral and continuous rectangular, as seen looking onto said first surface.

18. An X-ray analysis apparatus according to claim 16 wherein said target material is provided by a plurality of wires supported in said target.

19. An X-ray analysis apparatus according to claim 16 having means for displacing said target relative to said charged particle beam, thereby to expose a fresh portion of said track to said beam.

20. An X-ray analysis apparatus according to claim 16 wherein said detector produces signals in accordance with the transmitted X-rays detected and the apparatus further comprises (d) a collimator for said transmitted X-rays located in front of said detector, (e) scanning means for rotating a
said test piece relatively to said target and said detector, and (f) data processing means for processing data
in said signals from said detector in accordance with the principle of computer tomography.

21. An X-ray analysis apparatus according to claim 16 wherein said detector is an X-ray-sensitive film.

22. A target for X-ray generating apparatus adapted to bombarded by an energy beam and having a first side at which said energy beam is incoming and opposite said first side a second side at which X-rays are emitted, said target having an element made of X-ray generating material exposed at both said first side and said second side of the target, said element having a narrow elongate shape and being arranged in said target as a non-circular track.

23. A target according to claim 22 wherein said element has a shape selected from spiral shape and continuous rectangular shape, as seen looking onto said first surface.

24. A target according to claim 22 wherein said element has a width of less than 1 mm in the direction transverse to its direction of elongation.

* * * * *